(12) United States Patent
Rezkallah

(10) Patent No.: US 8,664,436 B2
(45) Date of Patent: Mar. 4, 2014

(54) PROCESS FOR THE SEPARATION OF ORGANIC ACIDS AND AMINO ACIDS FROM FERMENTATION BROTHS

(75) Inventor: Areski Rezkallah, Chauny (FR)

(73) Assignee: Rohm and Haas Company, Philadelphia, PA (US)

( * ) Notice: Subject to any disclaimer, the term of this patent is extended or adjusted under 35 U.S.C. 154(b) by 451 days.

(21) Appl. No.: 12/980,566

(22) Filed: Dec. 29, 2010

(65) Prior Publication Data

US 2011/0160483 A1    Jun. 30, 2011

(30) Foreign Application Priority Data

Dec. 29, 2009   (FR) .................................... 09 290999

(51) Int. Cl.
*C07C 51/47* (2006.01)
*C07C 209/86* (2006.01)
*C12P 7/56* (2006.01)
*C12P 13/14* (2006.01)

(52) U.S. Cl.
USPC ............ 562/589; 562/553; 562/607; 562/608

(58) Field of Classification Search
None
See application file for complete search history.

(56) References Cited

U.S. PATENT DOCUMENTS 3,655,746 A    4/1972   Tetsuya et al.
5,068,418 A    11/1991  Kulprathipanja et al.

FOREIGN PATENT DOCUMENTS

| CN | 101376628 | 3/2009 |
|---|---|---|
| EP | 0486024 A2 | 5/1991 |
| GB | 939573 | 10/1963 |

OTHER PUBLICATIONS

Database WPI—Mar. 4, 2009 (Thomson Scientific, London GB).

*Primary Examiner* — Yevegeny Valenrod
(74) *Attorney, Agent, or Firm* — Carl P. Hemenway

(57) ABSTRACT

The present invention relates to a solid bed adsorptive separation of organic acid and/or amino acids from fermentation broths containing organic acid and/or amino acid.

7 Claims, 2 Drawing Sheets

PROCESS FOR THE SEPARATION OF ORGANIC ACIDS AND AMINO ACIDS FROM FERMENTATION BROTHS

This patent application claims the benefit of the earlier filed European Patent Application serial number 09290999.3 filed on Dec. 29, 2009.

The present invention relates to a solid bed adsorptive separation of organic acid and/or amino acids from fermentation broths containing organic acid and/or amino acid.

Organic acid is used as a food acidulant and flavoring and in pharmaceutical, plastics, textiles and other industrial formulations. The increased use of food and pharmaceutical products formulated with organic acid has been primarily responsible for growth of worldwide production of organic acid to greater than 300 million pounds per year which is expected to continue in the future.

Traditionally, organic acid is produced by a submerged culture fermentation process which employs molasses, potatoes or starch as feed and a microorganism, e.g., *Lactobacillus del brueckii, L. bulgarcius* or *L. leichnanii*. The fermentation product contains carbohydrates, amino acids, proteins and salts as well as organic acid, which must be separated from the fermentation broth.

Typically during the separation of organic acid, calcium salt is precipitated. The resulting calcium carboxylate is filtered to remove heavy metals and some organic impurities. The regenerated organic acid is separated from the precipitated $CaSO_4$, e.g., by filtration, and the resulting crude organic acid is then purified by carbon treatment and sodium ferrocyanide to remove additional organic impurities and heavy metals, respectively. After filtration, the organic acid is contacted with an ion exchange resin to remove trace ions. The purification process is complex and high purity is often difficult to obtain.

U.S. Pat. No. 5,068,418 discloses a process for separating lactic acid from fermentation broths by employing a non-zeolite polymeric adsorbent, which selectively adsorbs lactic acid. The non-zeolite polymeric adsorbent comprises a weakly basic anionic exchange resin possessing tertiary amine or pyridine functional groups, or a strongly basic anionic exchange resin possessing quaternary amine functional groups and mixtures thereof. The problem with the separation process of U.S. Pat. No. 5,068,418 is that it discloses the use of mineral acid. Mineral acid contributes to contamination of lactic acid. Purity is thus affected by the elution solution. Sulfuric acid, the mineral acid disclosed in U.S. Pat. No. 5,068,418 affects the operating capacity of the resin which in turn directly affects operating costs. Once saturated by the mineral acid, the resin has to be regenerated. For highly concentrated solutions, the resin has to be frequently regenerated; hence directly increasing process costs. Thus what is needed is a process which will raise efficiency thereby reducing costs.

The present invention solves this problem by providing a process for separating organic and amino acids from fermentation broths without the need of minerals acid solution.

Figure 1:
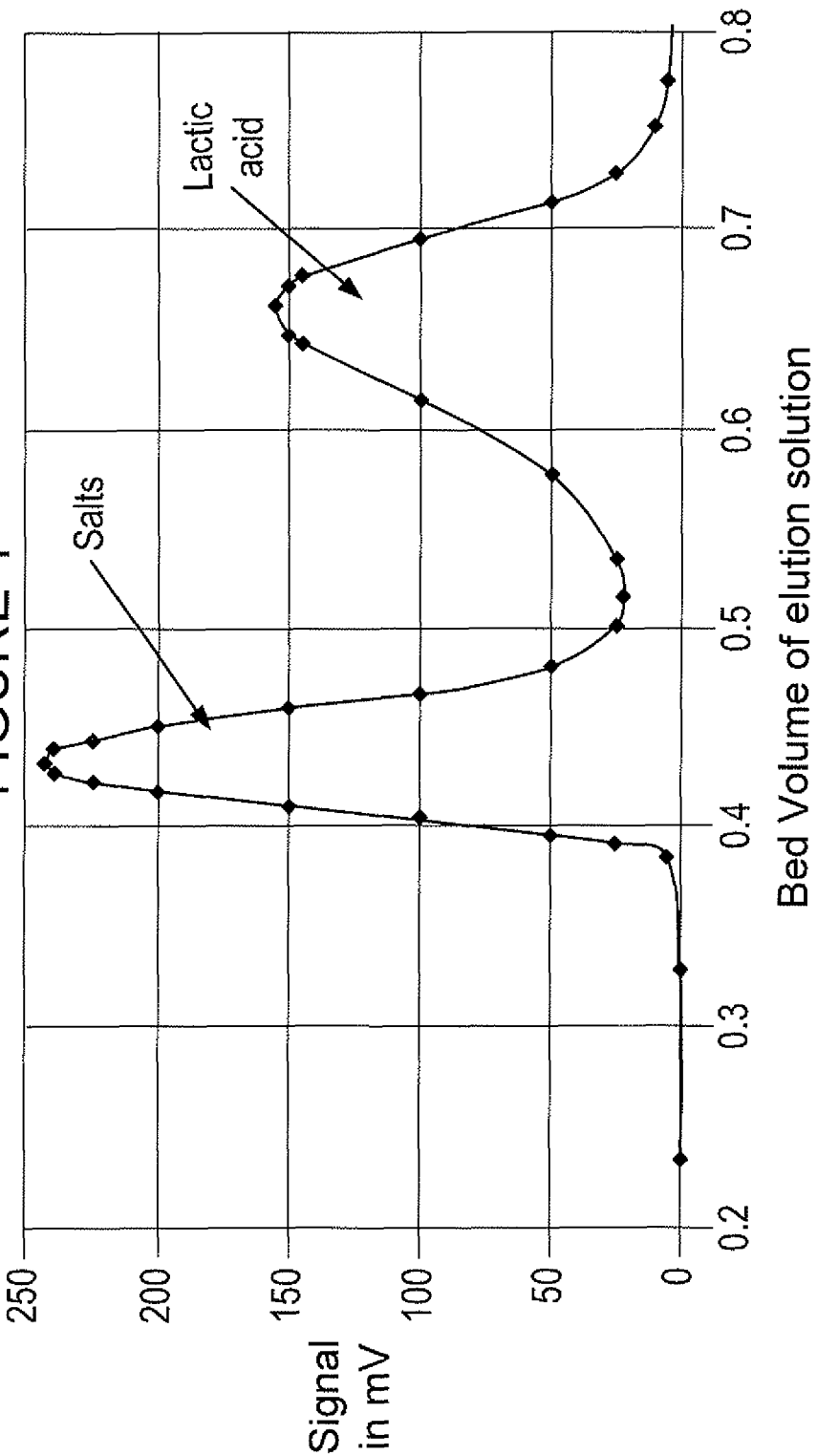
FIG. 1 illustrates a chromatographic separation of lactic acid and salt using a strong acid cation exchange resin.

The present invention relates to a process for the separation of organic acids from fermentation broths comprising:

i) providing a feed material comprising a fermentation product further comprising an organic acid;
ii) providing an ion exchange adsorbent media; and
iii) separating the organic acid from the feed material by eluting the feed material with a mobile phase through the ion exchange adsorbent media; wherein
the mobile phase is selected from the group consisting of dilute organic acid and water.

Additionally, the present invention relates to Å process for the separation of amino acids from fermentation broths comprising:

i) providing a feed material comprising a fermentation product;
ii) providing an ion exchange adsorbent media; and
iii) separating the amino acid from the feed material by eluting the feed material with a mobile phase through the ion exchange adsorbent media; wherein
the mobile phase is selected from the group consisting of dilute amino acid and water.

As used herein by "organic acid" is meant an acid that contains in its formula carbon, hydrogen, and oxygen and wherein the carbon and oxygen form a carboxyl group. Non-limiting examples of organic acids include lactic, acetic, formic, oxalic, and citric acids. Organic acids as defined herein also include the class of amino acids. As used herein "organic acids" may be in acid form or their corresponding salt form.

As used herein by "amino acid" is meant an organic acid that contains an amine group in its formula. Non-limiting examples of amino acids include glutamic and aspartic acids. "Amino acids" may be in acid form or corresponding salt form.

The feed material contemplated in this invention is a fermentation product. Common non-limiting fermentation products useful in the present invention are obtained from the submerged culture fermentation of sugars (e.g. glucose), molasses, potatoes or, especially, starch by one of the microorganism, *Lactobacillus del brueckii, L. bulgarcius* or *L. leichnanii*. Nonionized organic acid will be separated from other ionic species (including organic anions) in the fermentation broths using the resin adsorbents herein described.

The separation of organic acid can be enhanced significantly by adjusting the pH of the feed to a level below the ionization constant of organic acid. The ionization constant (pKa) of organic acid is 3.86, Handbook of Chemistry & Physics), 53rd Edition, 1972-3, CRC Press, and, therefore, the pH of the organic acid feed and the adsorption zone should be below 3.86.

The solid bed adsorptive separation of organic acid and/or amino acids from fermentation broths is accomplished by employing adsorbent resins. The resins of the invention can be gellular (or "gel-type") or "macroreticular" as the term is used in some recent literature, namely, Kunin and Hetherington, A Progress Report on the Removal of Colloids From Water by Macroreticular Ion Exchange Resins, paper presented at the International Water Conference, Pittsburgh, Pa., October 1969, reprinted by Rohm & Haas Co. In recent adsorption technology, "the term microreticular refers to the gel structure per se, size of the pores which are of atomic dimensions and depend upon the swelling properties of the gel" while "macroreticular pores and true porosity refer to structures in which the pores are larger than atomic distances and are not part of the gel structure. Their size and shape are not greatly influenced by changes in the environmental conditions such as those that result in osmotic pressure variations" while the dimensions of gel structure are "markedly dependent upon the environmental conditions." In "classical adsorption", "the terms macroporous and macroporous normally refer to those pores less than 20 Å and greater than 200 Å, respectively. Pores of diameters between 20 Å and 200 Å are referred to as transitional pores." The authors selected the term "macroreticular", instead, to apply to the new ion exchange resins used in this invention, which "have both a microreticular as well as a macroreticular pore structure. The former refers to the distances between the chains and crosslinks of the swollen gel structure and the latter to the pores that are not part of the actual chemical structure. The macroreticular portion of structure may actually consist of micro-, macro-, and transitional-pores depending upon the pore size distribution." (Quotes are from page 1 of the Kunin et al. article). The macroreticular structured adsorbents also have good resistance to attrition (not common to conventional macroreticular resins). In this application, therefore, all reference to "macroreticular" indicates adsorbent of the types described above having the dual porosity defined by Kunin and Hetherington. "Gel" and "gel-type" are used in their conventional sense.

The adsorbent resins of the present invention may be selected from one of the following classes of ion exchange resins: strong acid cationic, strong base anionic, weak base anionic, and weak acid cationic. Specifically, exchange resins possessing tertiary amine or pyridine functionality in acid form in a cross-linked polymeric matrix, e.g., acrylic or styrene are useful in the present invention. They are especially suitable when produced in bead form, have a high degree of uniform polymeric porosity, exhibit chemical and physical stability and good resistance to attrition. The adsorbents of the present invention are normally available in chloride form, but can be converted to the acid form. "Amberlite™" adsorbent resins, manufactured by the Rohm and Haas Company, are suitable. Specifically, non-limiting examples of useful resins for the present invention are Amberlite™ FPC23 H, CR1310, FPA53, FPA55, FPA53 and FPA54 adsorbent resins.

Suitable polymeric adsorbents in terms of structure and ionic form of the present invention will differ somewhat in physical properties such as porosity (volume percent), skeletal density and nominal mesh sizes, and perhaps more so in surface area, average pore diameter and dipole moment. Typically, the adsorbents of the present invention will have a surface area of 10-2000 $m^2/g$ and preferably from 100-1000 $m^2/g$; uniform particle coefficient from 1 to 1.6; particle size ranging from 200 to 800 microns, and alternatively from 300 to 600 microns.

In the process of the present invention the adsorbent is contacted with a feed mixture in a mobile phase. The feed mixture is composed of the fermentation broth. The mobile phase comprises a diluted solution of the organic acid to be purified or simply water as the eluent. Mineral acid is not used in the present invention. According to the present invention, the eluent is chosen according to the interaction between the functional groups of the feed stream organic or amino acid and ion exchange adsorbent media. Typically, water is the eluent or mobile phase when there is no ionic interaction between the media and the subject acid or salt. Conversely, when there is ionic interaction between the functional groups of organic acid or amino acid and media a dilute solution of the subject organic acid or amino acid, respectively, shall be used.

The feed mixture may be contacted with the adsorbent and mobile phase in a dense compact fixed bed. In the simplest embodiment of the invention the adsorbent is employed in the form of a single static bed in which case the process is only semicontinuous. In another embodiment a set of two or more static beds may be employed in fixed bed contacting with appropriate valving so that the feed mixture is passed through one or more of the other beds in the set. The flow of feed mixture may be either up or down. Any of the conventional apparatus employed in static bed fluid-solid contacting may be used.

Countercurrent moving bed or simulated moving bed countercurrent flow systems, however, have a greater separation efficiency than fixed adsorbent bed systems and are therefore another alternative. In the moving bed or simulated moving bed processes the adsorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in the above mentioned U.S. Pat. No. 2,985,589. Although both liquid and vapor phase operations can be used in many adsorptive separation processes, liquid-phase operation is preferred for this process because of the lower temperature requirements and because of the higher yields of extract product than can be obtained with liquid-phase operation over those obtained with vapor-phase operation. Adsorption conditions will include a temperature range of from 20° C. to 200° C., alternatively 20° C. to 25° C., or alternatively from 50° C. to 90° C., a pressure to ensure liquid phase, e.g. in the range of from about atmospheric to about 500 psig (3450 kPa gauge) with 50 psi to 100 psi being more preferred and a pH below the ionization constant (pKa) of organic acid.

DETAILED DESCRIPTION OF FIGURES

FIG. 1 illustrates a separation of a solution containing about 130 g/L of lactic acid and 70 g/L of salts with a strong acid cation in appropriate ionic form. A fraction of the solution was injected 1 ml injected into the column. Water was used as elution solution. The elution flow rate was 8 mL/min giving a linear velocity around 3 in/h. The outlet of the column was connected to a specific detector. The resolution was 3.39 and the overlay: 0.00.

Figure 2:
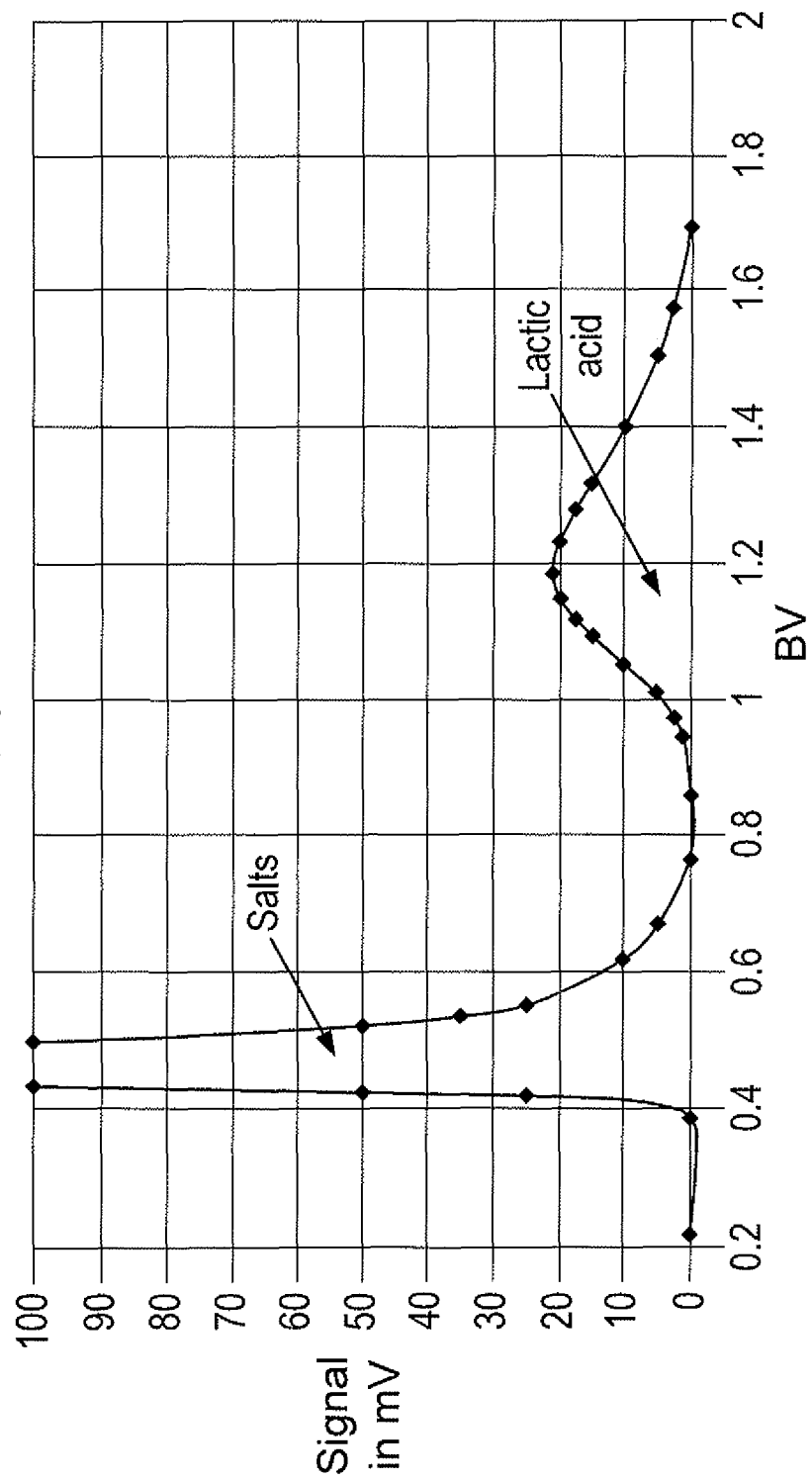
FIG. 2 illustrates a chromatographic separation of lactic acid and salt using a weak base anion exchange resin.

FIG. 2 illustrates the separation of a solution containing about 130 g/L of lactic acid and from 70/L of salts with a weak base anion in appropriate ionic form. A fraction of the solution was injected. Diluted lactic acid at a concentration of 0.02 N was used as elution solution. The elution flow rate was 8 mL/min giving a linear velocity around 3 m/h. The outlet of the column was connected to a specific detector. The resolution was 1.69 and the overlay: 0.00.

I claim:

1. A process for the separation of organic acids from fermentation broths comprising:
   i) providing a feed material comprising a fermentation product further comprising an organic acid;
   ii) providing an ion exchange adsorbent media; and
   iii) separating the organic acid from the feed material by eluting the feed material with a mobile phase through the ion exchange adsorbent media;
wherein there is ionic interaction between the organic acid and the ion exchange adsorbent media, and the mobile phase is a dilute solution of the organic acid.

2. The process of claim 1 wherein the organic acid is lactic acid.

3. The process of claim 1 wherein the organic acid is acetic acid.

4. The process of claim 1 further wherein the separating the organic acid from the feed material by eluting the teed material with a mobile phase through the ion exchange adsorbent media is conducted in a simulated moving bed.

5. A process for the separation of amino acids from fermentation broths comprising:
   i) providing a feed material comprising a fermentation product;
   ii) providing an ion exchange adsorbent media; and
   iii) separating the amino acid from the feed material by eluting the feed material with a mobile phase through the on exchange adsorbent media;
wherein there is ionic interaction between the amino acid and the ion exchange adsorbent media, and the mobile phase is a dilute solution of the amino acid.

6. The process of claim 5 wherein the amino acid is sodium glutamate.

7. The process of claim 5 further wherein the separating the amino acid from the feed material by eluting the feed material with a mobile phase through the ion exchange adsorbent media is conducted in a simulated moving bed.

* * * * *